United States Patent [19]

Burba et al.

[11] 4,156,779
[45] May 29, 1979

[54] PIPERAZINE AND PIPERIDINE ENAMINES HAVING AN HYDROXY GROUP

[75] Inventors: Christian Burba, Ascheberg-Herbern; Hans-Guenter Volland, Unna, both of Fed. Rep. of Germany

[73] Assignee: Schering Aktiengesellschaft, Berlin and Bergkamen, Fed. Rep. of Germany

[21] Appl. No.: 898,948

[22] Filed: Apr. 21, 1978

[30] Foreign Application Priority Data

Apr. 26, 1977 [DE] Fed. Rep. of Germany ....... 2718393

[51] Int. Cl.$^2$ .................... C07D 211/08; C07D 241/04
[52] U.S. Cl. ..................................... 544/358; 544/386; 544/402; 546/247
[58] Field of Search ............................. 544/358, 386; 260/293.86, 293.88; 546/247

[56] References Cited

U.S. PATENT DOCUMENTS 3,250,794  5/1966  Mod ..................................... 260/404
3,357,978  12/1967  Thominet .......................... 260/247.1
3,865,791  2/1975  Brinkmann .................. 260/77.5 CH

OTHER PUBLICATIONS

Wagner et al., "Synthetic Organic Chemistry," Wiley and Sons, Inc., N. Y., 1953, p. 567.

*Primary Examiner*—Donald G. Daus
*Assistant Examiner*—Lisa Jones
*Attorney, Agent, or Firm*—Curtis, Morris & Safford

[57] ABSTRACT

What is disclosed is the method of making a monoenamine having a free hydroxy group which comprises reacting a lactone or a carboxylic acid containing an hydroxy group with an amine selected from the group consisting of 2-methyl piperazine, 1-(2-aminoethyl)-piperazine, 4-aminomethyl-piperidine, or 2,3-dimethyl-3-(gamma-aminopropyl)-piperidine to form the corresponding secondary amine containing an hydroxy group and then reacting said secondary amine with an aliphatic aldehyde or cyclic ketone to form said monoenamine.

6 Claims, No Drawings

PIPERAZINE AND PIPERIDINE ENAMINES HAVING AN HYDROXY GROUP

The present invention relates to mono-enamines having an hydroxy group and to methods for making the same.

U.S. Pat. No. 3,865,791 granted Feb. 11, 1975 teaches prepolymers containing enamine groups, which prepolymers are formed by the reaction of a polyisocyanate and an enamine having at least one hydroxy group. Such prepolymers are made by first reacting an aliphatic aldehyde or cyclic ketone with a compound having at least one secondary amino group and at least one hydroxy group. (A monoenamine comprising 1-(2-hydroxyethyl)-piperazine is taught as a particularly suitable.) The reaction is optionally catalyzed by acid and may be carried out with heating or cooling. The water of reaction and excess carbonyl compounds are removed. The compound so obtained is then reacted in a second step with an amount of polyisocyanate equivalent to the hydroxy hydrogen.

The present invention relates to mono-enamines having at least one hydroxy group which are suitable for use in forming prepolymers such as are taught in U.S. Pat. No. 3,865,791. More in particular, such compounds are obtained by reacting a carboxylic acid containing an hydroxy group, or by reacting a lactone, with 1-(2-aminoethyl)-piperazine (NAEP), 2-methylpiperazine, 4-aminomethyl-piperidine, or 2,3-dimethyl-3-(γ-aminopropyl)-piperidine, to obtain the corresponding secondary amines containing an hydroxy group, and then reacting the compounds so obtained with an aliphatic aldehyde or cyclic ketone.

Hydroxystearic acid, ricinoleic acid, and, in particular, ε-caprolactone, are preferred carboxylic acids containing hydroxyl groups and a preferred lactone.

The reaction of lactones with organic compounds containing hydroxy or amino groups as an initiator is well known. Despite the addition of a catalyst and considerable reaction temperatures, amino groups can only be reacted in this way in comparatively long reaction times (cf. German Auslegeschrift DT-AS No. 1,206,586). Also, the reaction of amines with molar amounts of caprolactone at high temperature is known. According to DT-AS No. 1,211,652, this reaction, however, takes place with participation of the hydroxy groups, so that aminocarboxylic acid amides are formed as products:

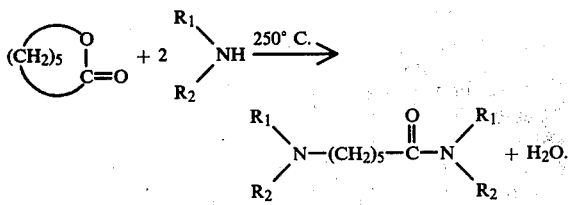

If the reaction takes place with primary aliphatic amines in the presence of water at increased pressure (cf. DT-AS No. 1,265,159), no open chain product, but a substituted caprolactam, is instead produced according to:

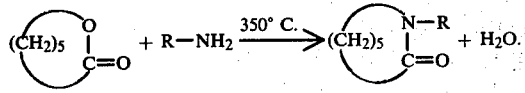

For the corresponding reaction with an ammonium salt, ε-hydroxycapronamide is formulated as an intermediate stage:

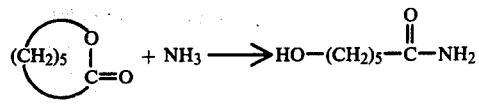

It must be considered surprising that NAEP, 2-methylpiperazine, 4-aminomethyl-piperidine, or 2,3-dimethyl, 3-(γ-aminopropyl)-piperidine can be reacted with carboxylic acids containing hydroxy groups, or with lactones, in a directed amidation reaction, with retention of the secondary amino groups, to obtain secondary amines containing hydroxyl groups or, by further reaction, to obtain the corresponding enamines.

The working method of the invention permits the preparation of enamines containing amide groups with only very small amounts of ketimines or aldimines.

The first reaction step is exemplified below with ε-caprolactone and NAEP:

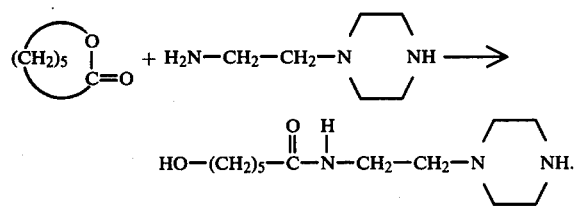

The reaction of NAEP with ε-caprolactone leads to a new substance having the molecular formula $C_{12}H_{35}N_3O_2$ and is of special interest. It is especially economical since both reagents are produced on a large industrial scale.

The reaction of NAEP, 2-methylpiperazine, 4-aminomethyl-piperidine, or 2,3-dimethyl-3-(γ-aminopropyl)piperidine with the acid components according to the invention takes place on heating, either with or without the addition of water. It is also possible to heat the amine components and to add the acid components together with water.

A further reaction possibility involves the use of an azeotrope, for example xylene as the entraining agent, and the possible use of a catalyst, whereby, under good conditions, a complete reaction can be achieved.

Suitable acid components containing hydroxy groups are as follows: hydroxystearic acid, ricinoleic acid, and those hydroxy acids which under condensation conditions do not enter into any side reactions such as dehydration. Suitable lactones are those having moderate ring size which, upon breaking of the ring with the amine components, yield defined derivatives of the corresponding hydroxy acids, for example butyrolactone, valerolactone, caprolactone and, in particular, ε-caprolactone. Suitable amine components are, as set forth above, NAEP, 2-methyl-piperazine, 4-aminomethyl-piperidine, or 2,3-dimethyl-3-(γ-aminopropyl)-piperidine. However, in principle, the acid components can also be reacted with analogous diamines the amino groups of which have differing reactivities.

The preparation of the enamines takes place by combining the secondary amine with an excess of carbonyl component and, following the addition of a suitable entraining agent (toluene or xylene), heating under nitrogen in a water separator until the separation of water is completed. In some cases, the carbonyl component itself can serve as the entraining agent.

The reaction product can be used directly after removing excess carbonyl components and solvent.

Aliphatic aldehydes and cyclic ketones are particularly suitable as carbonyl components. Examples of aldehydes and ketones which can advantageously be used for the preparation of enamines are: acetaldehyde, propionaldehyde, n-butyraldehyde, iso-butyraldehyde, diethylacetaldehyde, cyclopentanone, trimethylcyclopentanone, cyclohexanone, trimethylcyclohexanone, and other substituted cyclohexanones and cyclopentanones.

Examples of organic diisocyanates which can be reacted with the enamine compounds are aromatic polyisocyanates such as 2,4- and 2,6-toluene diisocyanate, 4,4'-diisocyanatodiphenylmethane, and 1,5-naphthylenediisocyanate; aliphatic diisocyanates such as hexamethylene-diisocyanate, trimethyl hexamethylene diisocyanate, and dimeryl diisocyanate ("dimeryl" refers to a dimerized fatty acid group); cycloaliphatic diisocyanates such as dicyclohexyl methane diisocyanate and isophorone diisocyanate (=1-isocyanato-3-isocyanatomethyl-3,5,5-trimethyl-cyclohexane); triisocyanates containing biuret groups; the reaction products of polyisocyanates with polyols, for example low molecular weight aliphatic polyols or polybutadienediols; and prepolymeric isocyanates which are prepared by the reaction of excess diisocyanate and polyesters or polyethers.

For preparing isocyanate pre-adducts, linear or branched polypropylene glycols having an average molecular weight of 500 to 1000 are preferably used. The tri- or poly-isocyanates are preferably added such that the ratio of isocyanate groups to hydroxy groups is from 1.8 to 2.2.

In general it is purposeful to mix the components with cooling at 0° C.-30° C. and, optionally, to add a catalyst such as tin compounds or tertiary amines after the possibly exothermic reaction has died out. Subsequently, the mixture is warmed at an elevated temperature of, preferably, 50° C. to 100° C. for such a period until the analytically-determined isocyanate content corresponds to the calculated value.

The enamines containing hydroxy groups are mixed with the isocyanate adduct preferably in a NCO:OH ratio equal to 1. The addition must take place with vigorous stirring and, possibly, cooling to temperatures of 20° C.-30° C. The mixture is stirred until no free isocyanate can be detected by infrared spectroscopy.

Prepolymeric enamines prepared from the mono-enamines according to the invention form stable mixtures with organic polyisocyanates, which latter can optionally be capped. These mixtures can be used in the presence of water for the preparation of lacquers, casting compounds, patching compounds, and coatings (cf. U.S. Pat. No. 3,865,791).

A better understanding of the present invention and of its many advantages will be had by referring to the following specific Examples, given by way of illustration.

In the following Examples, the homogeneity of the reaction is analytically evident from the simultaneous observance of the hydroxy number, on the one hand, and, on the other hand, of the amine number (total amine number of primary-secondary-tertiary amine number).

When determining the hydroxy number, it is of course understood that primary or secondary amino groups also affected by acetylation must be taken into account.

The cleanest reaction is characterized by the smallest possible residual amount of primary amino groups and by an hydroxy number closest to the theoretical value.

The secondary amine number and hydroxy number are determined by difference.

EXAMPLE 1

Aminoamide from caprolactone and 1-(2-aminoethyl)-piperazine (NAEP)

142 g of N-aminoethylpiperazine are heated to 145° C. A mixture of 114 g of caprolactone and 36 g of water are added thereto dropwise over 2.5 hours. During the dosing, a portion of the water distills off. Subsequently, the mixture is stirred for an additional two hours at 150° C. For a further hour, the mixture is heated to 220° C.-230° C. and this temperature is then maintained for three hours. At the conclusion, the excess NAEP is distilled off at a maximum of 180° C. in a vacuum established by a water aspirator. The product so obtained has the following characterizing data:

Amine number (total)=424 (calculated=462)
Amine number (tertiary)=223 (calculated=231)
Amine number (primary)=22 (calculated=0)
Amine number (secondary)=179 (calculated=231)
Hydroxy number =238 (calculated = 231)
Acid number=1.0 (calculated=0)

EXAMPLE 2

Enamine from isobutyraldehyde and the aminoamide of Example 1

219 g of aminoamide, 120 ml of toluene, and 25 ml of a strongly acid cation exchange ("Lewatite S 100") are combined. While warming them to a mixture of 45° C., 87 g of isobutyraldehyde are added thereto. The reaction mixture is permitted to boil and in this way the water of reaction is separated. After about two hours, all the water has distilled off. The ion exchanger is separated by filtration and the solvent and excess aldehyde are distilled off. The highly viscous product obtained in this way has an amine number of 351 (calculated=378).

EXAMPLE 3

Aminoamide from caprolactone and NAEP

In variation of Example 1, 142 g of NAEP, 114 g of caprolactone, and 36 g of water are combined and the mixture is heated to 145° C. This temperature is maintained for about 4.5 hours and the mixture is then heated in a further hour to 220° C.-230° C. After three hours at this temperature, the excess NAEP is distilled off at a maximum of 180° C. in a vacuum established by a water aspirator. The product so obtained has the following characterizing data:

Amine number (total)=409 (calculated=462)
Amine number (tertiary)=222 (calculated=231)
Amine number (primary)=15 (calculated=0)
Amine number (secondary)=172 (calculated=231)
Hydroxy number=241 (calculated=231)
Acid number=1.0 (calculated=0)

EXAMPLE 4

Aminoamide from caprolactone and NAEP

In variation of Example 1, 142 g NAEP and 114 g of caprolactone are combined and the mixture is heated to 145° C.-150° C. This temperature is maintained for about 4.5 hours and the mixture is heated in a further hour to 220° C.-230° C. After three hours at this temperature, the excess NAEP is distilled off at a maximum of 180° C. in a vacuum from a water aspirator. The product so obtained has the following characterizing data:
Amine number = (total) = 416 (calculated = 462)
Amine number = (tertiary) = 225 (calculated = 231)
Amine number = (primary) = 21 (calculated = 0)
Amine number (secondary) = 170 (calculated = 231)
Hydroxy number = 236 (calculated = 231)
Acid number = 0.8 (calculated = 0).

EXAMPLE 5

Aminoamide from caprolactone and NAEP, in variation of Example 1 using xylene as an entraining agent 142 g of NAEP (1 mol + 10 percent excess), 0.25 g of $H_3PO_4$, 2 g of water, and 65 ml of xylene are combined and heated to reflux (about 160° C.) Subsequently, 114 g of caprolactone (1 mol) are added dropwise over two hours, whereupon the temperature falls to 145° C. This temperature is maintained for two hours and then, by distilling off the xylene, the mixture is heated over a period of three hours to 220° C. and is maintained for three hours at this temperature. In the vacuum established by a water aspirator and at a maximum temperature of 180° C., the excess NAEP is distilled off. The product thus obtained has the following characterizing data:
Amine number (total) = 430 (calculated = 462)
Amine number (tertiary) = 229 (calculated = 231)
Amine number (primary) = 22 (calculated = 0)
Amine number (secondary) = 179 (calculated = 231)
Hydroxy number = 236 (calculated = 231)
Acid number = 0.8 (calculated = 0)

EXAMPLE 6

Aminoamide from hydroxystearic acid and NAEP 154.2 g of 12-hydroxystearic acid (saponification number = 181.6; acid number = 172) are combined with 64.5 g of N-aminoethylpiperazine [amine number (total) = 1266; amine number (tertiary) = 416; about 0.8 percent diethylene triamine according to gas chromatographic evaluation] and are reacted, with stirring, for eight hours at a maximum of 220° C. Subsequently, the reaction product is maintained for an additional 2.5 hours at a maximum of 180° C. in the vacuum from a water aspirator. A product having the following characterizing data is obtained:
Amine number (tertiary) = 239 (calculated = 268)
Amine number (tertiary) = 125 (calculated = 134)
Amine number (primary) = 14 (calculated = 0)
Amine number (secondary) = 100 (calculated = 134)
Hydroxy number = 119 (calculated = 134)
Acid number = 0.33 (calculated = 0)

EXAMPLE 7

Aminoamide from caprolactone and 2-methylpiperazine 114 g of caprolactone, 112.5 g of 2-methylpiperazine(amine number = 1098), and 36 g of water are combined and the mixture is heated to reflux for five hours at a temperature of about 150° C. In a further two hours, the temperature is raised to 220° C. with separation of distillate and is held for about four hours at this temperature. Subsequently, the excess 2-methylpiperazine is removed at a maximum temperature of 180° C. using the vacuum from a water aspirator. A product having the following characterizing data is obtained:
Amine number = 227 (calculated = 260)
Hydroxy number = 226 (calculated = 260)

EXAMPLE 8

(a) Aminoamide from caprolactone and 2,3-dimethyl-3-(γ-aminopropyl)piperidine 187 g of the amine are warmed to 145° C. A mixture of 114 g of caprolactone and 36 g of water is added thereto dropwise over a period of 2.5 hours. During the dosing, a portion of the water distills over. The mixture is then stirred for an additional two hours at 150° C. The mixture is heated, in a further hour, to 220° C.-230° C. and this temperature is then maintained for three hours. At the end, the excess amine is distilled off at a maximum temperature of 220° C. in a water-aspirator vacuum. The product obtained in this way has the following characteristics:
Amine number (total) = 195 (calculated = 197)
Amine number (primary) = 2.8 (calculated = 0)
Amine number (secondary) = 192.2 (calculated = 197)
Hydroxy number = 171 (calculated = 197)
Acid number = 2.5 (calculated = 0).

(b) Enamine from isobutyraldehyde and the aminoamide of part (a)

232 g of the aminoamide prepared in part (a), 100 ml of toluene, and 4 g of a strongly acid ion exchanger ("Dowex 50×8", anhydrous) are warmed to 45° C. while 89 g of isobutyraldehyde (about 50% excess) are added thereto. The reaction mixture is left to boil and in this way the reaction water is separated. After the water separation is concluded, the ion exchanger is separated by filtration and the solvent is distilled off from the filtrate together with excess aldehyde. The highly viscous product so obtained has an amine number = 160 (calculated = 165).

EXAMPLE 9

(a) Aminoamide from caprolactone and 4-aminomethylpiperidine 119.7 g of 4-aminomethylpiperidine are heated to about 145° C. At this temperature, a mixture of 114 g of caprolactone and 36 g of water is added dropwise. During the dosing, a portion of the water distills off. Subsequently, the mixture is stirred for two hours at 150° C. In a further hour, the mixture is heated to 220° C.-230° C. and this temperature is then maintained for three hours. At the end, the excess of 4-aminomethylpiperidine is distilled off in a water aspirator vacuum. The product so obtained has the following characterizing data:
Amine number (total) = 196 (calculated = 246)

Amine number (primary)=20.0 (calculated=0)
Hydroxy number=248 (calculated=246)
Acid number=1.5 (calculated=0)

(b) Enamine from isobutyraldehyde and the aminoamide of part (a)

200 g of the aminoamide described above in (a) are combined in about 120 ml of toluene, after the addition of 3.5 g "Dowex 50 W(36)X W 8" (anhydrous), with 97 g of isobutyraldehyde (about 50 percent excess, as in Example 8b). A highly viscous product having an amine number=157 (calculated=165) is obtained.

EXAMPLE 10

(a) Aminoamide from ricinoleic acid and NAEP 298 g of technical ricinoleic acid (acid number=179, saponification number=188, hydroxy number=164) are combined with 131 g of N-aminoethylpiperazine [amine number (total)=1266; amine number (tertiary)=416; about 0.8% diethylene triamine according to gas chromatographic evaluation] and brought to reaction by heating to a maximum of 200° C. for eight hours with stirring. Subsequently, the reaction product is held for an additional 2.5 hours at a maximum temperature of 180° C. in the vacuum from a water aspirator. A product with the following characteristics was obtained:

Amine number (total)=224 (calculated=275)
Amine number (tertiary)=136 (calculated=137)
Amine number (primary)=15.1 (calculated=0)
Hydroxy number=139 (calculated=137)
Acid number=0.6 (calculated=0)

(b) Enamine from the product of 10 (a) and 3,3,5-trimethylcyclohexanone (TMCO)

400 g of the reaction product from Example 10 (a) are combined with 163 g of TMCO, 2 g of a strongly acid anhydrous ion exchanger, and 150 ml of xylene and the mixture is heated to reflux using a water separator. After about 10 hours the reaction is concluded. The ion exchanger is separated by filtration and xylene and excess TMCO are removed in vacuum at a maximum temperature of 180° C.

A viscous reaction product having a total amine number of 192 is obtained. The amine number for further reaction is 85, as determined from this and the ratio of the primary amine number and the secondary amine number to the total amine number of the aminoamide employed.

What is claimed is:

1. A compound of the formula

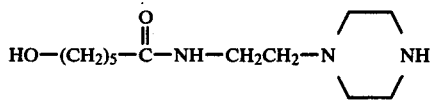

2. A compound of the formula

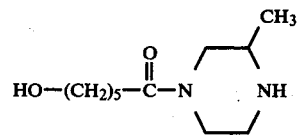

3. A compound of the formula

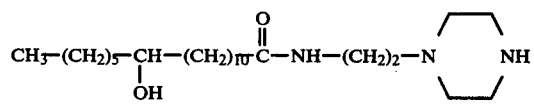

4. A compound of the formula

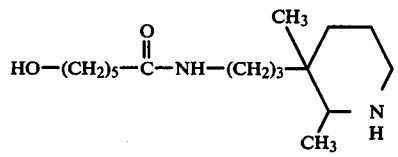

5. A compound of the formula

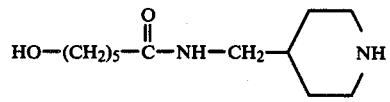

6. A compound of the formula

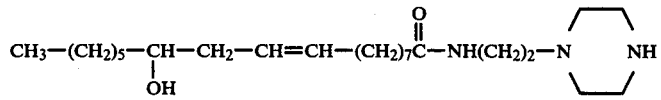

* * * * *